(12) United States Patent
Liu et al.

(10) Patent No.: US 10,995,126 B2
(45) Date of Patent: May 4, 2021

(54) IMMUNOGENIC PEPTIDE CONTAINING A B CELL EPITOPE OF TUMOR ASSOCIATED ANTIGEN L6

(71) Applicants: National Health Research Institutes, Miaoli County (TW); Academia Sinica, Taipei (TW)

(72) Inventors: Shih-Jen Liu, Miaoli County (TW); Hsin-Wei Chen, Miaoli County (TW); Steve Roffler, Taipei (TW); Ming-Hsi Huang, Miaoli County (TW); Chih-Hsiang Leng, Miaoli County (TW)

(73) Assignees: National Health Research Institutes, Miaoli County (TW); Academia Sinica, Taipei (TW)

( * ) Notice: Subject to any disclaimer, the term of this patent is extended or adjusted under 35 U.S.C. 154(b) by 155 days.

(21) Appl. No.: 16/098,735

(22) PCT Filed: May 3, 2017

(86) PCT No.: PCT/US2017/030805
§ 371 (c)(1),
(2) Date: Nov. 2, 2018

(87) PCT Pub. No.: WO2017/192697
PCT Pub. Date: Nov. 9, 2017

(65) Prior Publication Data
US 2019/0135883 A1    May 9, 2019

Related U.S. Application Data

(60) Provisional application No. 62/331,698, filed on May 4, 2016.

(51) Int. Cl.
*A61K 38/00* (2006.01)
*C07K 14/47* (2006.01)
*A61P 35/00* (2006.01)
*A61K 39/00* (2006.01)
*A61K 39/39* (2006.01)

(52) U.S. Cl.
CPC .......... *C07K 14/4748* (2013.01); *A61K 38/00* (2013.01); *A61K 39/001102* (2018.08); *A61K 39/39* (2013.01); *A61P 35/00* (2018.01); *A61K 2039/55561* (2013.01); *A61K 2039/55566* (2013.01); *A61K 2039/572* (2013.01); *C07K 2319/00* (2013.01)

(58) Field of Classification Search
CPC ................ C07K 14/4748; A61K 38/00; A61K 39/001102; A61P 35/00
See application file for complete search history.

(56) References Cited

U.S. PATENT DOCUMENTS

| 5,200,508 | A | 4/1993 | Nilaver et al. |
| 5,314,995 | A | 5/1994 | Fell et al. |
| 5,354,847 | A | 10/1994 | Liu et al. |
| 5,597,707 | A | 1/1997 | Marken et al. |
| 5,645,835 | A | 7/1997 | Fell et al. |
| 7,368,527 | B2 * | 5/2008 | Rosen .................... A61K 38/17 530/300 |
| 8,465,756 | B2 | 6/2013 | Liu et al. |
| 2007/0032413 | A1 | 2/2007 | Rosen et al. |
| 2011/0038894 | A1 | 2/2011 | Liu et al. |

FOREIGN PATENT DOCUMENTS

WO    WO-2015/054427 A1    4/2015

OTHER PUBLICATIONS

Lin et al. "Chimeric peptide containing both B and T cells epitope of tumor-associated antigen L6 enhances anti-tumor effects in HLA-A2 transgenic mice". Cancer Letters 377 (2016) 126-133.
Marken et al. "Cloning and Expression of the Tumor-Associated Antigen L6" Proceedings of the National Academy of Sciences USA vol. 89, pp. 3503-3507, 1992.
Sher et al "A HLA-A2-Restricted CTL Epitope Induces Anti-Tumor Effects Against Human Lung Cancer in Mouse Xenograft Model", Impact Journals, Oncotarget vol. 7, No. 1, Nov. 26, 2015.
Tu et al "A Novel HLA-A2-restricted CTL Epitope of Tumor-associated Antigen L6 can Inhibit Tumor Growth In Vivo" J Immunother, vol. 35, No. 3, Apr. 2012.
Visintin et al "Novel Anti-TM4SF1 Antibody-Drug Conjugates with Activity against Tumor Cells and tumor Vasculature" Molecular Cancer Therapeutics, 14(8), Aug. 2015.

* cited by examiner

*Primary Examiner* — Sheela J. Huff
(74) *Attorney, Agent, or Firm* — Cesari & McKenna, LLP

(57) ABSTRACT

Described herein are an immunogenic peptide containing the sequence of CLDSLGQWN (SEQ ID NO:2) and a method of using the peptide for treating cancer.

17 Claims, 10 Drawing Sheets
Specification includes a Sequence Listing.

A

B

A

B

A

B

SEQUENCE LISTING

```
<160> NUMBER OF SEQ ID NOS: 22

<210> SEQ ID NO 1
<211> LENGTH: 202
<212> TYPE: PRT
<213> ORGANISM: Homo sapiens
<220> FEATURE:
<221> NAME/KEY: MISC_FEATURE
<222> LOCATION: (1)..(202)
<223> OTHER INFORMATION: TAL6

<400> SEQUENCE: 1

Met Cys Tyr Gly Lys Cys Ala Arg Cys Ile Gly His Ser Leu Val Gly
 1               5                  10                  15

Leu Ala Leu Leu Cys Ile Ala Ala Asn Ile Leu Leu Tyr Phe Pro Asn
                20                  25                  30

Gly Glu Thr Lys Tyr Ala Ser Glu Asn His Leu Ser Arg Phe Val Trp
            35                  40                  45

Phe Phe Ser Gly Ile Val Gly Gly Gly Leu Leu Met Leu Leu Pro Ala
        50                  55                  60

Phe Val Phe Ile Gly Leu Glu Gln Asp Asp Cys Cys Gly Cys Cys Gly
65                  70                  75                  80

His Glu Asn Cys Gly Lys Arg Cys Ala Met Leu Ser Ser Val Leu Ala
                85                  90                  95

Ala Leu Ile Gly Ile Ala Gly Ser Gly Tyr Cys Val Ile Val Ala Ala
            100                 105                 110

Leu Gly Leu Ala Glu Gly Pro Leu Cys Leu Asp Ser Leu Gly Gln Trp
        115                 120                 125

Asn Tyr Thr Phe Ala Ser Thr Glu Gly Gln Tyr Leu Leu Asp Thr Ser
    130                 135                 140
```

```
Thr Trp Ser Glu Cys Thr Glu Pro Lys His Ile Val Glu Trp Asn Val
145                 150                 155                 160

Ser Leu Phe Ser Ile Leu Leu Ala Leu Gly Gly Ile Glu Phe Ile Leu
                165                 170                 175

Cys Leu Ile Gln Val Ile Asn Gly Val Leu Gly Gly Ile Cys Gly Phe
                180                 185                 190

Cys Cys Ser His Gln Gln Gln Tyr Asp Cys
        195                 200
```

```
<210> SEQ ID NO 2
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 2

Cys Leu Asp Ser Leu Gly Gln Trp Asn
1               5
```

```
<210> SEQ ID NO 3
<211> LENGTH: 20
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid

<400> SEQUENCE: 3

Xaa Xaa Xaa Xaa Xaa Xaa Xaa Cys Leu Asp Ser Leu Gly Gln Trp Asn
1               5                   10                  15

Xaa Xaa Xaa Xaa
            20
```

```
<210> SEQ ID NO 4
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 4

Gly Leu Ala Glu Gly Pro Leu Cys Leu Asp Ser Leu Gly Gln Trp Asn
1               5                   10                  15

Tyr Thr Phe Ala
            20
```

```
<210> SEQ ID NO 5
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 5

Leu Leu Met Leu Leu Pro Ala Phe Val
1               5
```

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Arg Phe Val Trp Phe Phe Ser Gly Ile
1               5

<210> SEQ ID NO 7
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 7

Ala Lys Phe Val Ala Ala Trp Thr Leu Lys Ala Ala Ala
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 8

Ala Gln Tyr Ile Lys Ala Asn Ser Lys Phe Ile Gly Ile Thr Glu Leu
1               5                   10                  15

<210> SEQ ID NO 9
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 9

Ala Lys Phe Val Ala Ala Trp Thr Leu Lys Ala Ala Ala Ala Ala Ala
1               5                   10                  15

Leu Leu Met Leu Leu Pro Ala Phe Val Ala Ala Gly Leu Ala Glu
            20                  25                  30

Gly Pro Leu Cys Leu Asp Ser Leu Gly Gln Trp Asn Tyr Thr Phe Ala
            35                  40                  45

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
tcgtcgtttt gtcgttttgt cgtt                                              24

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11

-continued gggggacgat cgtcgggggg                                          20

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12
ggggacgacg tcgtgggggg g                                        21

<210> SEQ ID NO 13
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 13
tcgcgacgtt cgcccgacgt tcggta                                   26

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14
tcgtcgtttt cggcgcgcgc cg                                       22

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 15
tcgtcgtcgt tcgaacgacg ttgat                                    25

<210> SEQ ID NO 16
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 16
tcgcgaacgt tcgccgcgtt cgaacgcgg                                29

<210> SEQ ID NO 17
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 17

Ser Leu Gly Gln Trp Asn Tyr Thr Phe Ala Ser Thr Glu Gly Gln Tyr
1               5                   10                  15

Leu Leu Asp Thr
            20

```
<210> SEQ ID NO 18
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 18

Ser Thr Glu Gly Gln Tyr Leu Leu Asp Thr Ser Thr Trp Ser Glu Cys
1               5                   10                  15

Thr Glu Pro Lys
            20

<210> SEQ ID NO 19
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 19

Ser Thr Trp Ser Glu Cys Thr Glu Pro Lys His Ile Val Glu Trp Asn
1               5                   10                  15

Val Ser Leu Phe Ser
            20

<210> SEQ ID NO 20
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 20

Ala Lys Phe Val Ala Ala Trp Thr Leu Lys Ala Ala Ala Ala Ala Ala
1               5                   10                  15

Leu Leu Met Leu Leu Pro Ala Phe Val
            20                  25

<210> SEQ ID NO 21
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 21

Ala Lys Phe Val Ala Ala Trp Thr Leu Lys Ala Ala Ala Ala Ala Ala
1               5                   10                  15

Gly Leu Ala Glu Gly Pro Leu Cys Leu Asp Ser Leu Gly Gln Trp Asn
            20                  25                  30

Tyr Thr Phe Ala
        35

<210> SEQ ID NO 22
<211> LENGTH: 24
<212> TYPE: PRT
<213> ORGANISM: Artificial Sequence
<220> FEATURE:
<223> OTHER INFORMATION: Synthetic polypeptide
```

```
<400> SEQUENCE: 22

Ala Lys Phe Val Ala Ala Trp Thr Leu Lys Ala Ala Ala Ser Ser Cys
1               5                   10                  15

Ser Ser Cys Pro Leu Ser Lys Ile
            20
```

IMMUNOGENIC PEPTIDE CONTAINING A B CELL EPITOPE OF TUMOR ASSOCIATED ANTIGEN L6

CROSS-REFERENCE TO RELATED APPLICATIONS

This application is the National Stage of International Application No. PCT/US2017/030805, filed May 3, 2017, which claims the benefit of U.S. Provisional Application No. 62/331,698, filed May 4, 2016. The contents of both applications are hereby incorporated by reference in their entirety.

BACKGROUND

Tumor associated antigen L6 (TAL6) is a cell surface protein of the transmembrane-4 superfamily (TM4SF), also known as TM4SF1. TM4SF proteins are over-expressed in different types of human cancers including lung, breast, colon, prostate and liver cancer. TM4SF1-, TM4SF4- and TM4SF5-specific monoclonal antibodies can inhibit colon cancer growth, indicating that TM4SF proteins are crucial targets for cancer therapy. TAL6 is over-expressed in more than 80% of human lung, breast, colon and ovarian tumors but not normal tissues. Recently, TAL6 was found to play critical roles in cancer cell motility, invasion, metastasis and angiogenesis. It was previously demonstrated that an HLA-A2-restricted CTL epitope, A2-5, of TAL6 is capable of inducing CTL responses against cancer cells that express TAL6. In addition, the induced-CTL responses can be adoptively transferred to inhibit human lung cancer growth in immunocompromised mice.

SUMMARY

In one aspect, described herein in an immunogenic peptide that contains the sequence of CLDSLGQWN (SEQ ID NO: 2), wherein the peptide has 100 or fewer amino. In one embodiment, the peptide has the sequence of $X_1X_2X_3X_4X_5X_6X_7$CLDSLGQWN$X_8X_9X_{10}X_{11}$ (SEQ ID NO: 3), wherein $X_1$ to $X_{11}$, individually, is an amino acid (e.g., one of the 20 standard amino acids). For example, the peptide can include the sequence of GLAEGPLCLDSLGQWNYTFA (SEQ ID NO: 4). In one embodiment, the peptide further includes a cytotoxic T lymphocyte (CTL) epitope of TAL6 or a helper T cell (Th) epitope. In yet another embodiment, the peptide includes the sequence of AKFVAAWTLKAAAAAALLMLLPAFVAAAGLAEGPLCLDSLGQWNYTFA (SEQ ID NO: 9).

In another aspect, this disclosure includes a nucleic acid molecule containing a sequence that encodes the immunogenic peptide described herein.

In yet another aspect, described herein is an immunogenic composition containing the immunogenic peptide. The immunogenic composition can further include an adjuvant. The adjuvant can be selected from the group consisting of incomplete Freund's adjuvant (IFA), DOTAP, PELC, and unmethylated CpG-containing oligodeoxynucleotides (CpG). In one embodiment, the CpG is a Toll-like receptor 9 (TLR9) agonist. In one embodiment, the immunogenic composition includes both PELC and the CpG.

In one aspect, a method of treating a cancer in a subject in need thereof is described herein. The method includes administering to the subject the immunogenic composition described herein.

The details of one or more embodiments are set forth in the accompanying drawing and the description below. Other features, objects, and advantages of the embodiments will be apparent from the description and drawing, and from the claims.

DETAILED DESCRIPTION

Figure 1:
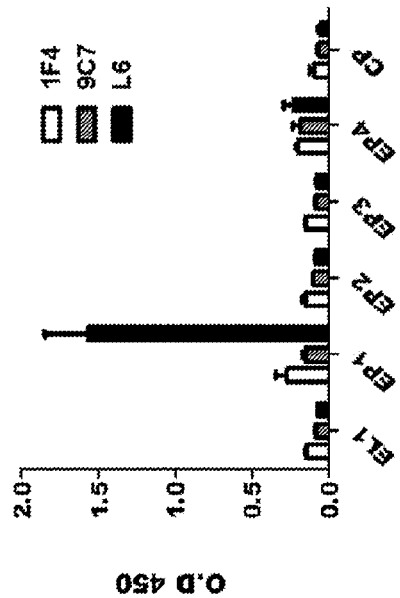
FIG. 1 includes (A) a scheme showing the overlapping peptides that cover the extracellular domains of TAL6: EL1 (residues 31 to 46 of SEQ ID NO: 1); EL2 (residues 114 to 164 of SEQ ID NO: 1); EP1 (SEQ ID NO: 4); EP2 (SEQ ID NO: 17); EP3 (SEQ ID NO: 18); and EP4 (SEQ ID NO: 19); and (B) a graph showing binding of the peptides to anti-TAL6 antibodies. A 96-well plate was coated with the indicated peptides (10 µg/ml) in each well. Three anti-TAL6 antibodies (1:500) were used to detect these peptides. CP: Control peptide.

It was unexpectedly discovered that TAL6 contains a B cell epitope that can induce antibody-dependent cellular cytotoxicity (ADCC) and anti-tumor effects in vivo.

Shown below is an amino acid sequence of TAL6 (SEQ ID NO: 1):

```
MCYGKCARCI GHSLVGLALL CIAANILLYF PNGETKYASE

NHLSRFVWFF SGIVGGGLLM LLPAFVFIGL EQDDCCGCCG

HENCGKRCAM LSSVLAALIG IAGSGYCVIV AALGLAEGPL

CLDSLGQWNY TFASTEGQYL LDTSTWSECT EPKHIVEWNV

SLFSILLALG GIEFILCLIQ VINGVLGGIC GFCCSHQQQY

DC
```

TAL6 contains two extracellular loops, i.e., EL1 (a.a. 31-a.a. 46 of SEQ ID NO: 1) and EL2 (a.a. 114-a.a. 164 of SEQ ID NO: 1). A B cell epitope is located within EL2.

Accordingly, described herein is an immunogenic peptide that includes the epitope, which contains the sequence of CLDSLGQWN (SEQ ID NO: 2). The immunogenic peptide can have 100 or fewer amino acids (e.g., 9, 10, 11, 12, 13, 14, 15, 20, 25, 30, 35, 40, 45, 50, 55, 60, 65, 70, 75, 80, 85, 90, 95, or 100 amino acids).

The peptide can have the sequence of $X_1X_2X_3X_4X_5X_6X_7$CLDSLGQWN$X_8X_9X_{10}X_{11}$ (SEQ ID NO: 3), in which $X_1$ to $X_{11}$, individually, is an amino acid. The term "amino acid" refers to any of the 20 standard amino acids (i.e., alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine). The term can also refer to a non-standard, non-proteinogenic, or chemically-modified amino acid, or an amino acid analog.

In one embodiment, the immunogenic peptide has the sequence of GLAEGPLCLDSLGQWNYTFA (SEQ ID NO: 4).

The immunogenic peptide can be a chimeric peptide that contains the above-described B cell epitope of TAL6 and one or more other peptide moieties. For example, the chimeric peptide can further contain an epitope of a non-TAL6 antigen or a helper T cell-stimulating epitope, or both. The chimeric peptide can also contain another epitope of TAL6 (e.g., another B cell epitope or a T cell epitope). Exemplary epitopes of TAL6 are described in U.S. Pat. No. 8,465,756.

Other peptide moieties that can be present in the chimeric peptide include one or more of an affinity tag (e.g., FLAG, poly-His, Myc, HA, CBP, HBH, or V5), a signal sequence (e.g., aleader sequence or a localization signal), a targeting peptide (for targeting the chimeric peptide to specific cells, cellular locations, or tissues), a ligand (e.g., a receptor ligand), and a therapeutic peptide.

In one embodiment, the chimeric peptide contains the sequence of SEQ ID NO: 2, 3, or 4, and one or both of a cytotoxic T lymphocyte (CTL) epitope of TAL6 and a helper T cell (Th) epitope. The CTL epitope can be LLMLLPAFV (SEQ ID NO: 5) or RFVWFFSGI (SEQ ID NO: 6). The Th epitope can be the PADRE peptide, e.g., AKFVAAWTLKAAA (SEQ ID NO: 7), or a peptide from tetanus toxoid, e.g., AQYIKANSKFIGITEL (SEQ ID NO: 8). One exemplary chimeric peptide has the sequence of AKFVAAWTLKAAAAAALLMLLPAFVAAAGLAEGPLCLDSLGQWNYTFA (SEQ ID NO: 9). The epitopes in the chimeric peptides can be arranged in any order.

A linker, e.g., a flexible linker containing 1, 2, 3, 4, 5, 6, 7, 8, 9, 10, 11, 12, 13, 14, or 15 amino acids, can link two adjacent peptide moieties in the chimeric peptide. A skilled practitioner would be able to design suitable linkers.

Conventional methods, e.g., chemical synthesis or recombinant technology, can be used to make the immunogenic peptide.

The immunogenic peptide can also be conjugated to one or more non-peptide moieties to form an immunogenic peptide conjugate. Such non-peptide moieties include nucleic acid molecules, antibodies, proteins, carbohydrates, detectable labels (e.g., fluorescent, radioactive, or enzymatic labels), small molecule drugs, polymers (e.g., polyethylene glycol), solid supports (e.g., beads or nanoparticles), plant extract components, and microbial components. Other modifications such as modifications to side chains, amino acid substitutions, incorporation of unnatural amino acids and/or their derivatives during peptide synthesis can also be employed to, for example, increase the immunogenic peptide's stability and/or in vivo efficacy.

As the above-described immunogenic peptide includes a B cell epitope of TAL6, a cancer antigen, it can be used for enhancing immune responses (e.g., antibody-dependent cellular cytotoxicity responses) against a TAL6-positive cancer, e.g., lung cancer, colon cancer, breast cancer, ovarian carcinoma, gastric cancer, Kaposi's sarcoma, hepatoma, pancreatic cancer, cervical cancer, endometrial cancer, head and neck cancer, ovarian cancer, or prostate cancer.

The immunogenic peptide or an expression vector capable of expressing the immunogenic peptide can be mixed with a pharmaceutically acceptable carrier to form an immunogenic composition. The composition can be administered to a subject in need thereof to treat cancer or enhance immune responses.

The composition can be formulated with a pharmaceutically acceptable carrier such as a phosphate buffered saline, a bicarbonate solution, and/or an adjuvant. Suitable pharmaceutical carriers and diluents, as well as pharmaceutical necessities for their use, are known in the art. This composition may be prepared as an injectable, liquid solution, emulsion, or another suitable formulation.

Examples of adjuvants include, but are not limited to, alum-precipitate, Freund's complete adjuvant, Freund's incomplete adjuvant, monophosphoryl-lipid A/trehalose dicorynomycolate adjuvant, water in oil emulsion containing Corynebacterium parvum and tRNA, and other substances that accomplish the task of increasing immune response by mimicking specific sets of evolutionarily conserved molecules including liposomes, lipopolysaccharide (LPS), molecular cages for antigen, components of bacterial cell walls, and endocytosed nucleic acids such as double-stranded RNA, single-stranded DNA, and unmethylated CpG dinucleotide-containing DNA. Other examples include cholera toxin, E. coil heat-labile enterotoxin, liposome, immune-stimulating complex (ISCOM), immunostimulatory sequences oligodeoxynucleotide, and aluminum hydroxide. The composition can also include a polymer that facilitates in vivo delivery.

In one embodiment, the adjuvant is incomplete Freund's adjuvant (IFA), DOTAP or a DOTAP salt, PELC (an emulsion-type adjuvant containing a bioresorbable polymer, Span®85, and squalene), or unmethylated CpG-containing oligodeoxynucleotide (CpG), e.g., a toll-like receptor 9 (TLR9) agonist. A combination of one or more adjuvants can be included in the immunogenic composition.

TLR9 CpG agonists include, but are not limited to, 5'-tcgtcgttttgtcgttttgtcgtt-3' (SEQ ID NO: 10), 5'-ggGGGACGATCGTCggggggg-3' (SEQ ID NO: 11), 5'-gggGACGACGTCGTGggggg-3' (SEQ ID NO: 12), 5'-tcgcgacgttcgcccgacgttcggta-3' (SEQ ID NO: 13), 5'-tcgtcgttttcggcgcgcgccg-3' (SEQ ID NO: 14), 5'-tcgtcgtcgttcgaacgacgttgat-3' (SEQ ID NO: 15), and 5'-tcgcgaacgttcgccgcgttcgaacgcgg-3' (SEQ ID NO: 16). Bases in upper case letters are phosphodiesters. Bases in lower case letters are phosphorothioates.

An effective amount of the immunogenic composition may be administered parenterally, e.g., subcutaneous injection or intramuscular injection. Alternatively, other modes of administration including suppositories and oral formulations may be desirable. For suppositories, binders and carriers may include, for example, polyalkalene glycols or triglycerides. Oral formulations may include normally employed incipients such as pharmaceutical grades of saccharine, cellulose, magnesium carbonate and the like. These compositions take the form of solutions, suspensions, tablets, pills, capsules, sustained release formulations or powders.

The specific example below is to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are herein incorporated by reference in their entirety.

Example: Antigenic Peptides for Cancer Therapy

A B cell epitope of tumor-associated antigen L6 (TAL6) was identified that could induce antibody-dependent cellular cytotoxicity (ADCC) in vivo. The B cell epitope was combined with a cytotoxic T lymphocyte (CTL) and a helper T (Th) epitope to form a chimeric peptide. The chimeric peptide was formulated with different adjuvants to immunize HLA-A2 transgenic mice and its immunogenicity was evaluated. The chimeric peptide formulated with an emulsion type nanoparticle (PELC) adjuvant and a toll-like receptor 9 agonist (i.e., an unmethylated CpG-containing oligodeoxynucleotide (CpG)) induced the greatest ADCC and CTL responses. The induced anti-tumor immunity inhibited the growth of TAL6-positive cancer cells. Moreover, immunization with the chimeric peptide inhibited cancer cell migration in vitro and metastasis in vivo. These data suggest that a chimeric peptide containing both B and T cell epitopes of TAL6 formulated with PELC/CpG adjuvant can be used for cancer immunotherapy.

Identification of B Cell Epitopes of TAL6

Figure 2:
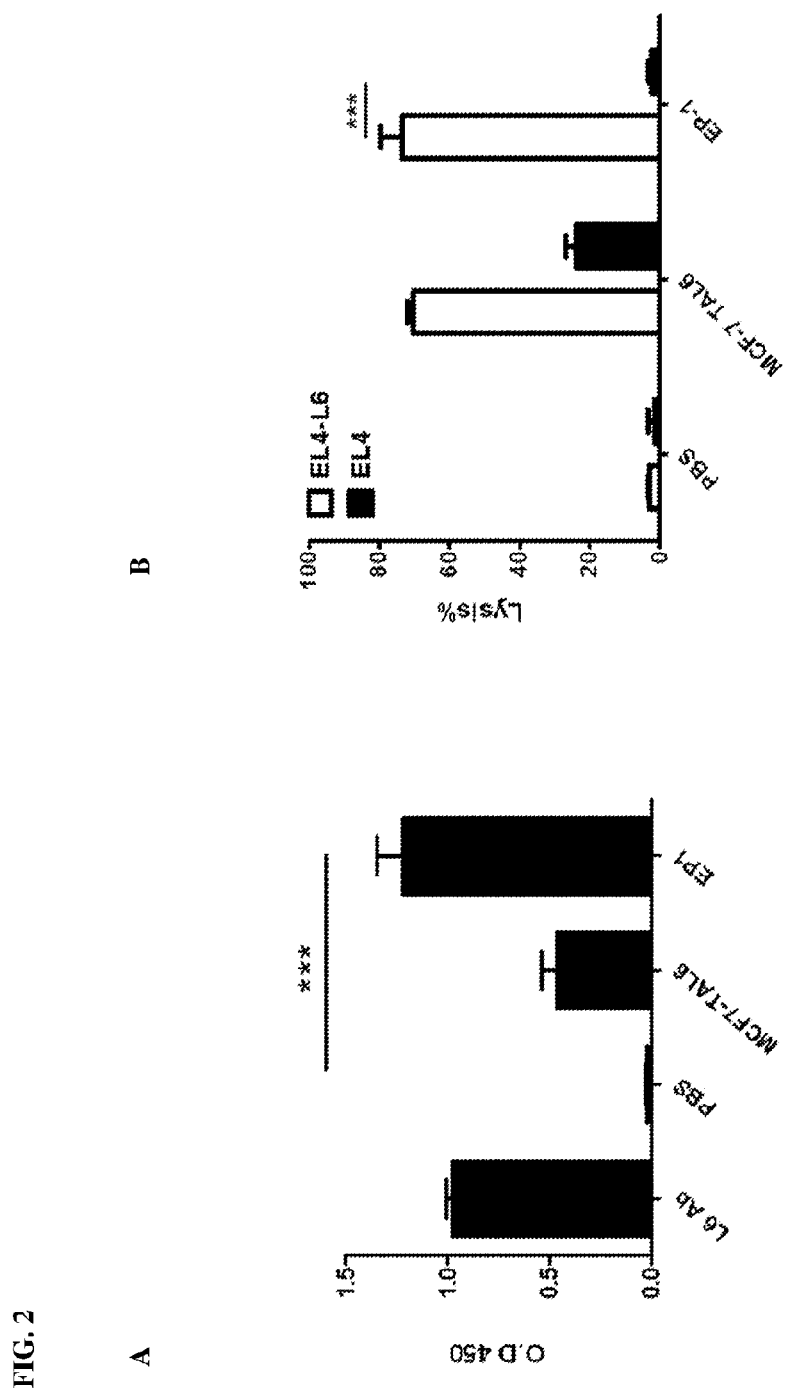
FIG. 2 is a set of graphs showing that immunization of WT mice with the EP1 peptide induced anti-tumor immunity. EP1 or positive control MCF-7/TAL6 cells formulated with incomplete Freund's adjuvant (IFA) were administered to mice twice at a two-week interval. (A) Anti-TAL6 antibody titers were determined by using cell-based ELISA. Antigen-specific antibody was calculated as: EL4-L6 (O.D.)–EL4 (O.D.). (B) TAL6-specific ADCC was determined in a $Cr^{51}$ release assay. The lysis percentage was calculated as immunized serum (lysis %)–naïve serum (lysis %). ***$P<0.001$.
Figure 3:
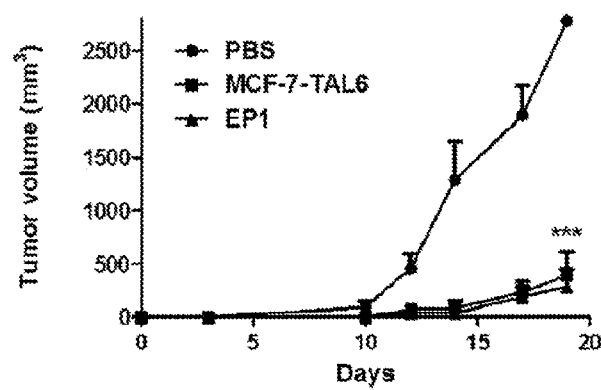
FIG. 3 is a set of graphs showing that immunization of WT mice with the EP1 peptide induced anti-tumor immunity. EP1 or positive control MCF-7/TAL6 cells formulated with incomplete Freund's adjuvant (IFA) were administered to mice twice at a two-week interval. (A) At 7 days after the final immunization, B16-L6 ($2 \times 10^4$) cells were inoculated subcutaneously. Tumor growth was monitored 2-3 times per week. (B) The survival rate of the mice was determined.
Figure 3:
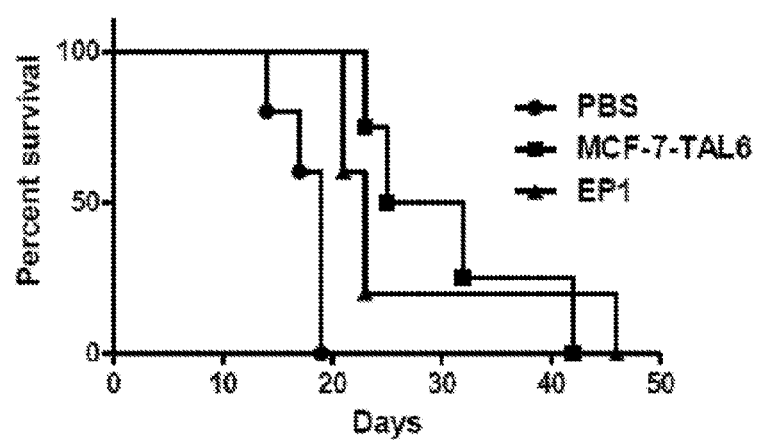

Three purified anti-TAL6 monoclonal antibodies (1F4, 9C7, L6) were used to detect the surface expression TAL6 on EL-4 (EL-4/L6) cells. See Chang et al., Int J Cancer, 116 (2005) 243-252. Serial diluted monoclonal antibodies bound EL-4/L6 cells but not negative control EL-4 cells (data not shown), confirming that these three monoclonal antibodies recognize an extracellular domain of TAL6. To further map the antibody-binding epitopes, five peptides (EL1 and EP1-4) that cover the EL1 and EL2 extracellular loops were used to determine the linear B cell epitopes using ELISA. See FIG. 1, A. Monoclonal antibody 1F4 and 9C7 did not recognize these peptides. By contrast, the EP1 peptide could be detected by L6 mAb. See FIG. 1, B To test whether the EP1 peptide could raise antibodies that bind native TAL6, the EP1 peptide or MCF-7/L6 cells (as positive control) were formulated with IFA/Th and administered to C57BL/6 mice. Sera from immunized mice were collected and the anti-TAL6 antibody titers were analyzed using cell-based ELISA. The sera (1:500) of mice immunized with EP1 or MCF-7/L6 cells had significantly higher amount of antibody than mice immunized with vehicle (PBS). See FIG. 2, A. Whether EP1 immunization could induce antibody-dependent cellular cytotoxicity (ADCC) was also investigated. Sera (1:100) from mice immunized with either EP1 or MCF-7/L6 cells could kill TAL6-expressed EL4 (EL4/L6) cells but not EL4 parental cells (61.82%±6.12% v.s. 0.36%±0.96% and 65.54%±1.77% v.s. 11.41%±3.094%). See FIG. 2, B. To investigate if the EP1 peptide could induce anti-tumor activity, mice were immunized with EP1 peptide and then challenged with B16-L6 cells ($2 \times 10^4$/mouse) at 7 days after the final immunization. Immunization of mice with either EP1 or MCF-7/L6 cells significantly inhibited tumor growth. See FIG. 3, A. The survival rates of mice are shown in FIG. 3, B. The data demonstrate that the EP1 peptide is a linear B cell epitope of TAL6 that has antitumor activity against cancer cells that express TAL6.

The EP1 Peptide Induced Anti-Tumor Effect in Mice Model

Figure 4:
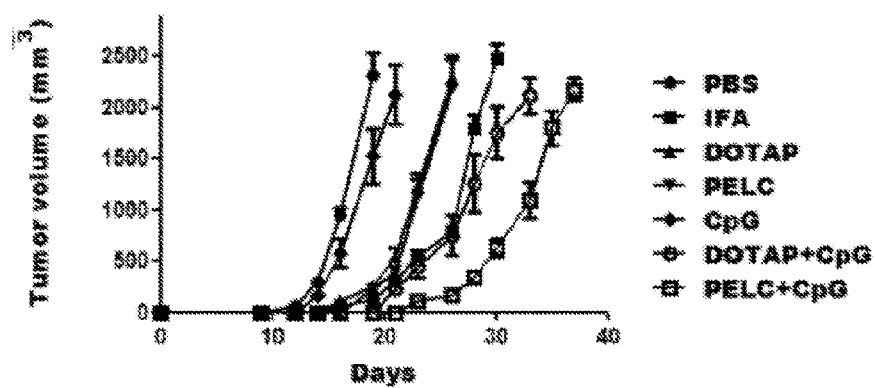
FIG. 4 is a set of graphs showing that EP1 formulated with PELC/CpG induced anti-tumor effects. Mice were immunized with 50 mg of EP1 formulated with the indicated adjuvants twice at a 14-day interval. (A) At 7 days after the second immunization, $2 \times 10^4$ of B16/TAL6 cells were injected subcutaneously. Tumor growth was monitored 2-3 times per week. Results obtained are expressed as mean SD (n=6). (B) Mouse survival rate was monitored. Results are expressed as means ±SD (*$P<0.05$.**$P<0.01$).
Figure 4:
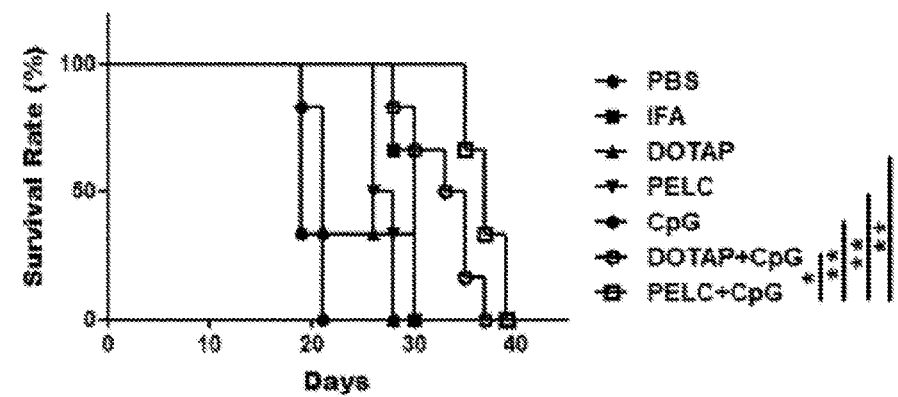

The EP1 peptide was formulated with different adjuvants. Mice were immunized with 50 mg of the formulations twice at a 14-day interval. At 7 days after the second immunization, 2×10⁴ B16/TAL6 cells were injected subcutaneously to the mice. Tumor growth was monitored 2-3 times per week. EP1 exhibited an anti-tumor effect. See FIG. 4, A. The survival rates are shown in FIG. 4, B.

Figure 5:
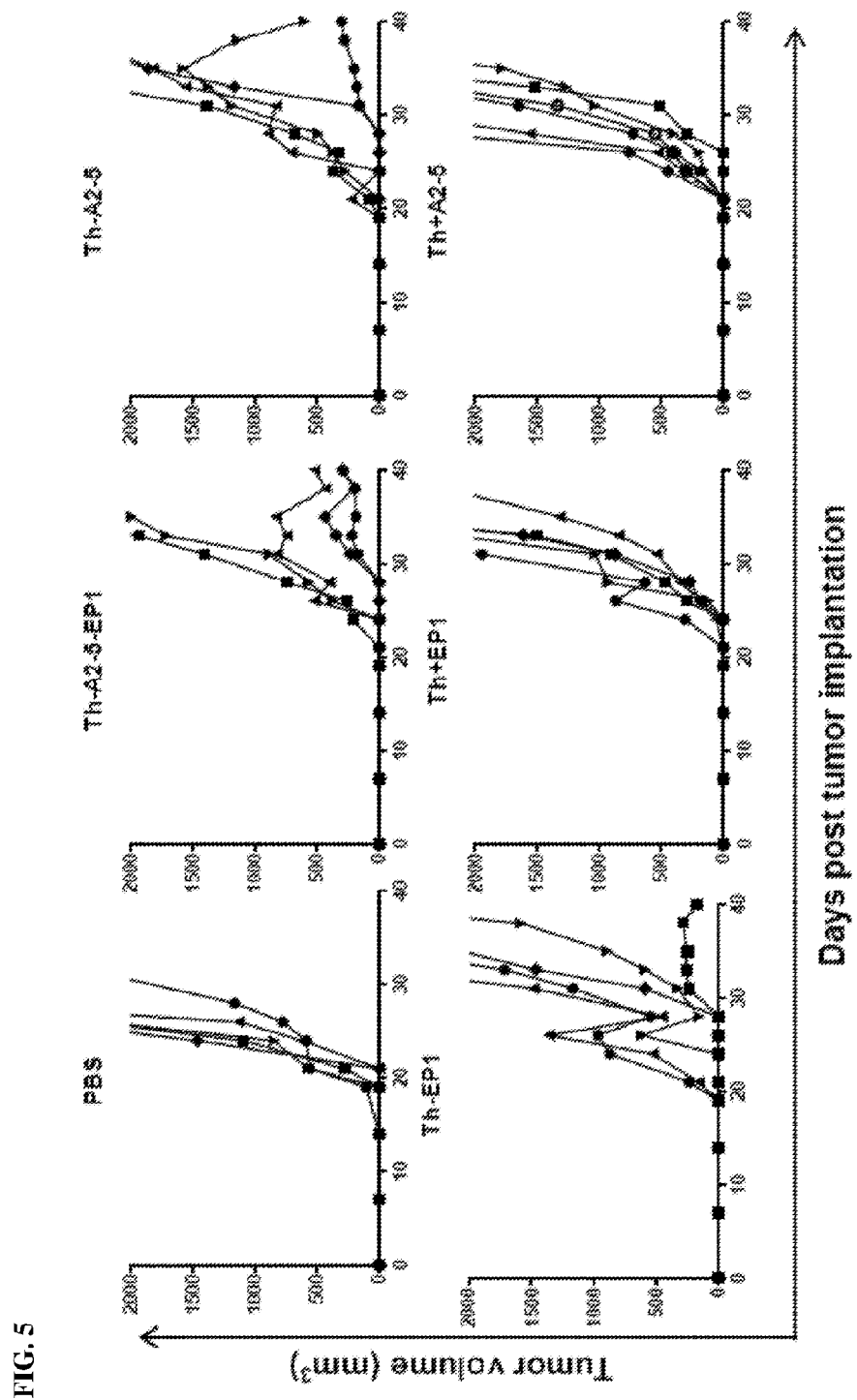
FIG. 5 is a set of graphs showing that the combination of T and B cell epitopes induced anti-tumor activity in HLA-A2 mice. Peptides (50 µg per mouse) formulated with incomplete Freund's adjuvant (IFA) were used to immunize HLA-A2 mice twice at a two-week interval. At 7 days after the final immunization, B16/L6/A2 cells ($2 \times 10^4$) were injected subcutaneously. Tumor size was monitored 2-3 times per week. Tumor volume=length×width×width/2. Each line in each graph corresponds to one animal (n=5-6).

A Chimeric Peptide Containing B and T Cells Epitopes Induced Greater Anti-Tumor Activity Than B or T Cell Epitopes Alone To investigate whether incorporation of a cytotoxic T cells (Tc) epitope can enhance the anti-tumor effects of B-cell epitope-based approaches, synthetic peptides Th-A2-5, Th-EP1, and Th-A2-5-EP1 were generated. See Table 1. The peptides were formulated with incomplete Freund's adjuvant (IFA) and used to immunize HLA-A2 transgenic (Tg) mice. Seven days after the final immunization, mice were subcutaneously injected with 2×10⁴ B16-L6-A2 cells. Tumor growth was monitored 2-3 times per week. Immunization with the chimeric Th-A2-5-EP1 peptide strongly inhibited tumor growth. See FIG. 5. The induction of both humoral and cellular immunity using chimeric peptide may synergize the anti-tumor activity.

TABLE 1

Synthetic peptides

| Name | Sequence |
|---|---|
| A2-5 | LLMLLPAFV (SEQ ID NO: 5) |
| EP1 | GLAEGPLCLDSLGQWNYTFA (SEQ ID NO: 4) |
| Th | AKFVAAWTLKAAA (SEQ ID NO: 7) |
| Th-A2-5 | AKFVAAWTLKAAAAAALLMLLPAFV (SEQ ID NO: 20) |
| Th-EP1 | AKFVAAWTLKAAAAAAGLAEGPLCLDSLGQWNYTFA (SEQ ID NO: 21) |
| Th-A2-5-EP1 | AKFVAAWTLKAAAAAALLMLLPAFVAAAGLAEGPLCLDSLGQWNYTFA (SEQ ID NO: 9) |
| Th-SCC | AKFVAAWTLKAAASSCSSCPLSKI (SEQ ID NO: 22) |

Chimeric Peptide Formulated with PELC/CpG Induced Strong Humoral and Cellular Anti-Tumor Immunity To investigate whether the Th-A2-5-EP1 chimeric peptide can induce A2-5-specific T cell responses, IFN-γ ELISPOT and CTL activity assays were performed. Th-A2-5-EP1 formulated with different adjuvants was administered to HLA-A2 transgenic mice twice at two weeks interval.

Figure 6:
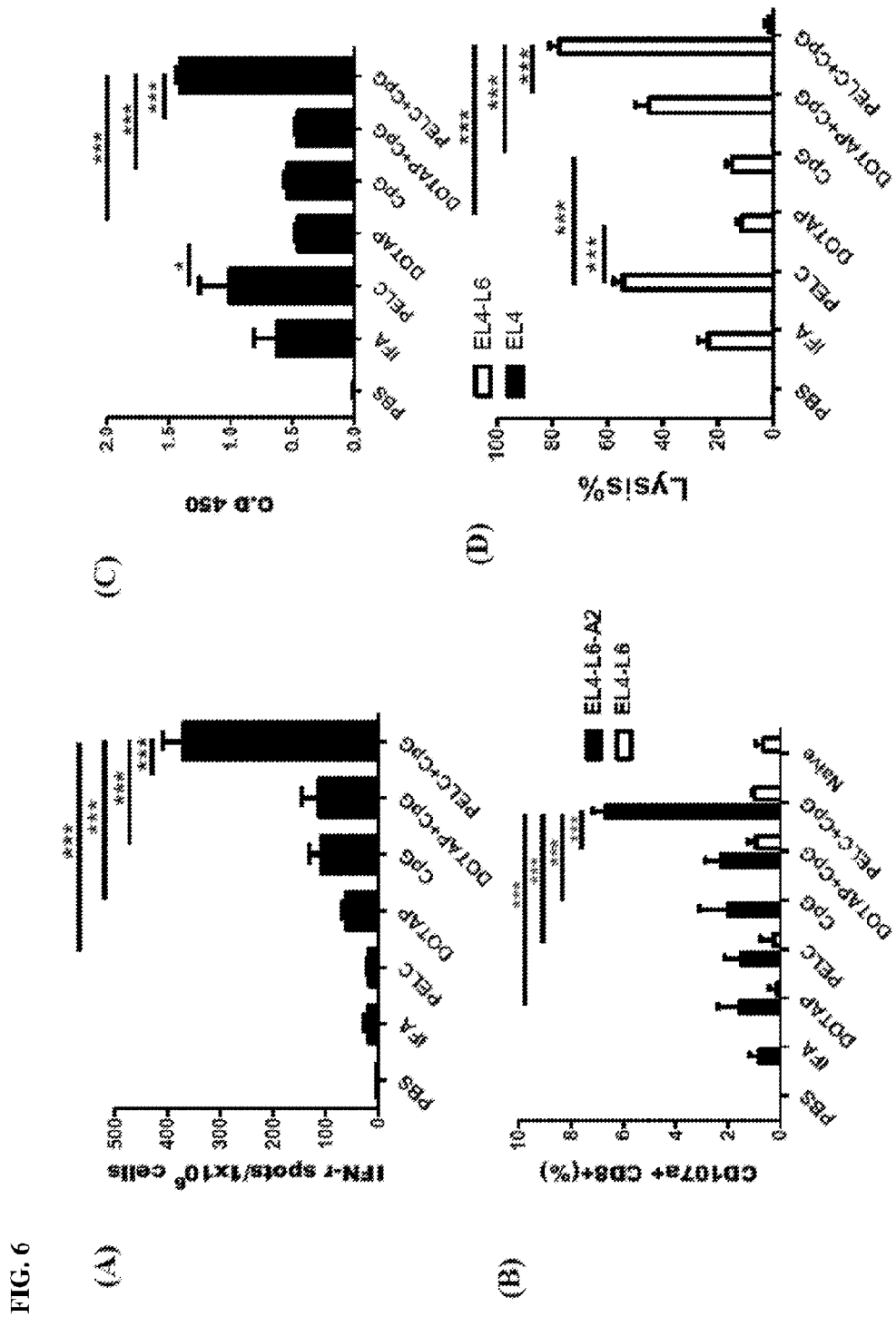
FIG. 6 is a set of graphs showing that immunization with PELC/CpG/Th-A2-5-EP1 induced high levels of humoral and cellular immunity in HLA-A2 mice. The Th-A2-5-EP1 peptide was formulated with different adjuvants. HLA-A2 transgenic mice were immunized with the different formulations twice at a 2-week interval. (A) IFN-γ-secreting cells were determined using IFN-γ ELISpot assay. Results are expressed as mean SD. *$P<0.001$. (B) Irradiated EL4-TAL6-A2 or EL4-TAL6 cells ($2 \times 10^4$) were used to stimulate splenocytes for 2 hr in the presence of anti-CD107a and anti-CD8 antibodies. *$P<0.001$. (C) Ten mg/ml of the EP1 peptide was coated on a 96-well ELISA plate and anti-sera from immunized mice (1:500) were added. *$P<0.05$. *$P<0.001$. (D) TAL6-specific ADCC was determined by Cr$^{51}$ release assay. The lysis percentage was calculated as: immunized serum (lysis %)—naïve serum (lysis %) *P<0.001.

IFN-γ-secreting cells from the mice were determined using the IFN-γ ELISPOT assay. Th-A2-5-EP1 formulated with PELC/CpG induced higher numbers of spots (368.5±40.42) than the peptide in other adjuvant formulations. See FIG. 6, A. A significant increase in the number of spots as compared to control mice were detected when Th-A2-5-EP1 peptide was formulated with DOTAP (60.5±7.85), CpG (107.2±23.89) or DOTAP/CpG (112.5±33.18) but not PELC (16.7±4.74) or IFA(18±9.75).

We conclude that Th-A2-5-EP formulated with PELC/CpG is capable of inducing strong A2-5-specific T cell responses.

To further determine if the PELC/CpG formulation can induce cytotoxic activity, the number of CD107a⁺CD8⁺ T cells was analyzed. Splenocytes from the mice were stimulated with irradiated EL4-L6-A2 or EL4-L6 cells for 2 hours in the presence of anti-CD107a and anti-CD8 antibodies. Th-A2-5-EP1 formulated with PELC/CpG induced higher numbers of CD107a⁺CD8⁺ T cells (6.69±0.49%) than did the other adjuvant formulations. See FIG. 6, B. These results demonstrated that Th-A2-5-EP1 formulated with PELC/CpG could induce strong and specific CTL responses.

Anti-sera from the mice were tested against EP1-coated 96-well ELISA plate. The Th-A2-5-EP1 peptide formulated with PELC containing CpG induced the highest IgG antibody amount against EP1 (O.D. 1.41±0.04). See FIG. 6, C. The PELC adjuvant induced higher antibody than the IFA adjuvant (O.D. 1.01±0.24 v.s. 0.622±0.183). See FIG. 6, C. Th-A2-5-EP1 peptide formulated with DOTAP liposomes, DOTAP/CpG or CpG alone produced similar level of antibody (O.D. 0.454±0.025, 0.46±0.02 and 0.54±0.02, respectively). See FIG. 6, C. In contrast to the antibody titer data, Th-A2-5-EP1 peptide formulated with PELC alone did not induce significant numbers of IFN-γ-secreting cells. See FIG. 6, B.

Sera from the immunized mice were used to evaluate ADCC activity. The Th-A2-5-EP1 peptide formulated with PELC/CpG induced the highest level of ADCC. See FIG. 6, D. The Th-A2-5-EP1 peptide formulated in the PELC adjuvant induced the second highest ADCC activity. These results correlated with the antibody titer data.

Figure 7:
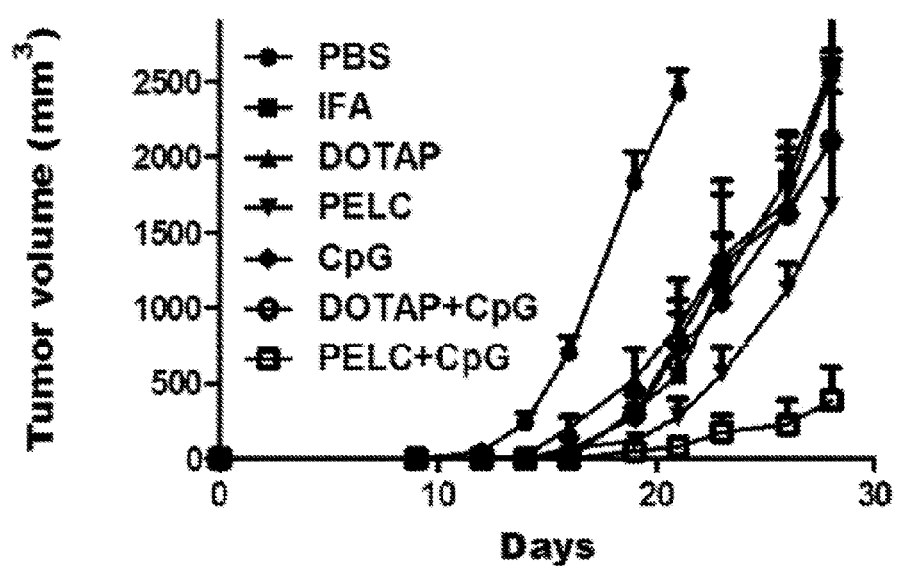
FIG. 7 is a graph showing that immunization with Th-A2-5-EP1 induced anti-tumor activity in HLA-A2 transgenic mouse. HLA-A2 transgenic mice were immunized with the Th-A2-5-EP1 peptide formulated in different adjuvants twice at a two-week interval. At 7 days after the final immunization, 2×10$^4$ of B16/TAL6/HLA-A2 cells were injected subcutaneously. Each group contained 6 mice. Tumor growth was monitored 2-3 times per week. Results are expressed as mean SD.

To evaluate the anti-tumor effects of Th-A2-5-EP in different adjuvant formulations, HLA-A2 transgenic mice were immunized with the formulations twice at a two-week interval. The mice were challenged with B16/L6/A2 cells (2×10⁴) at 7 days after the second immunization. Tumor growth was monitored 2-3 times per week. Th-A2-5-EP peptide formulated with PELC/CpG significantly inhibited tumor growth as compared to the other formulations. See FIG. 7. Th-A2-5-EP peptide formulated with IFA, DOTAP, PELC, CpG or DOTAP/CpG displayed moderate anti-tumor activity. See FIG. 7. The data demonstrated that a chimeric peptide containing Th, Tc and B cells epitopes formulated with PELC/CpG could induce strong humoral and cellular immunity against cancer.

Figure 8:
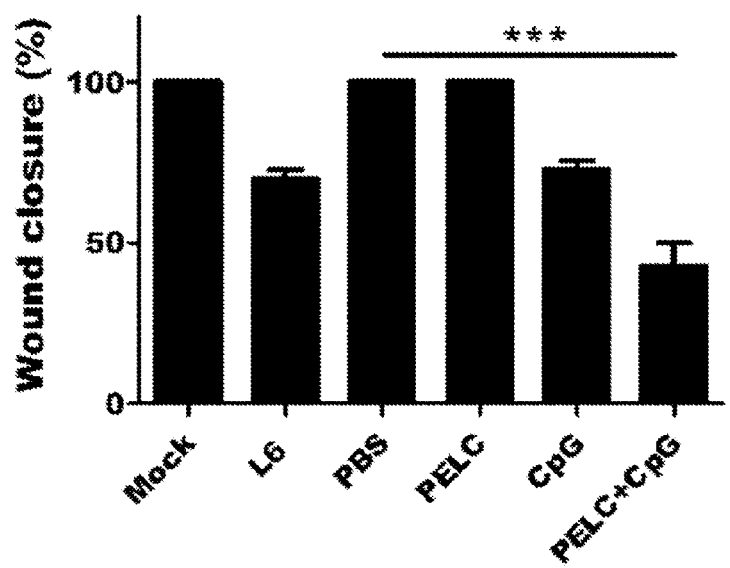
FIG. 8 is a graph showing that sera from immunized mice inhibited cancer cell migration. B16-L6 cells were cultured in a 24-well plate that contained one Culture-Insert (500 μm) in each well. After 24 h, the Culture-Inserts were removed and 100 ml of medium with or without antisera (1:100, v/v) from immunized mice was added. Images were acquired at 0, 24 and 48 h in vitro. L6 mAb (10 mg/ml) was used as a positive control. Cell migration into the defined cell free gap was observed at the indicated times under a microscope. Data are shown as mean±SD (n=5). Migration (%)=gap area at 48 hr/gap at 0 hr×100%. ***P<0.001.

Chimeric Peptide Th-A2-5-EP1 Formulated with PELC/CpG Inhibited Tumor Migration and Metastasis Whether sera from Th-A2-5-EP1 immunized mice could inhibit cancer cell migration was examined. A chambers wound assay was performed to evaluate the inhibition of cell migration. B16-L6 cell were cultured in 24-well plate with a CultureInsert (500 μm) for 24 hours. The Culture-Insert was then removed and 100 μl of medium, sera (1:100, v/v), or a positive control (L6 mAb) were added. Images acquired at 0, 24 and 48 hours showed inhibition of cancer cell migration after treatment with either L6 or serum from mice immunized with Th-A2-5-EP1 and PELC/CpG (data not shown). Quantification of the cell-free gap in three independent experiments revealed that sera from mice immunized with Th-A2-5-EP1 formulated with CpG alone (72.97%±5.97) or PELC/CpG (43.04%±15.47) significantly inhibited B16-L6 cell migration. See FIG. 8. Migration inhibition was not due to differences in cell proliferation (data not shown).

Inhibition of cancer cell migration suggested that cancer cell metastasis might also be inhibited by immunization with a chimeric peptide. The anti-metastasis activity of the peptide was examined in a B16-L6 metastasis mouse model. The Th-A2-5-EP1 peptide formulated with PELC, CpG, or PELC/CpG was used to immunize HLA-A2 transgenic mice twice at a two week interval. Seven days after the second immunization, B16-L6 cells ($5\times10^5$) were injected intravenously. At 22 days after cell inoculation, the mice were sacrificed and lung tissues were collected for analysis. Th-A2-5-EP1 formulated with PELC, CpG, or PELC/CpG dramatically reduced tumor nodule formation in lungs (data not shown). Interestingly, almost no tumor nodules were observed in mice immunized with the Th-A2-5-EP1 peptide formulated with PELC/CpG. The data demonstrated that Th-A2-5-EP1 formulated with PELC/CpG could inhibit cancer cell lung metastasis.

Figure 9:
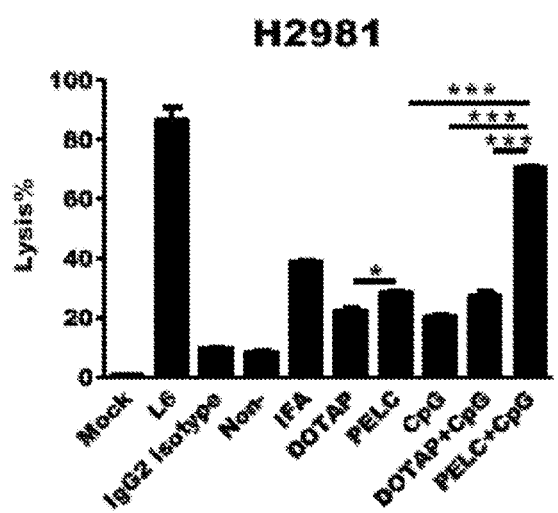
FIG. 9 is a set of graphs showing that peptide formulated with different adjuvants induced antibody-dependent cellular cytotoxicity (ADCC) against human cancer cells. Mice were immunized with peptide Th-EP1-A2-5 in various adjuvants twice at a two-week interval. Sera were collected at 6 weeks for ADCC assay. (A) Lung cancer cell line H2981 was used as a target. (B) Human breast cancer cell lines MCF7 and MCF7-TAL6 were used as targets. TAL6-specific ADCC was determined by Cr$^{51}$ release assay. The lysis percentage was calculated as: immunized serum (lysis %)–naïve serum (lysis %) ***P<0.001.
Figure 9:
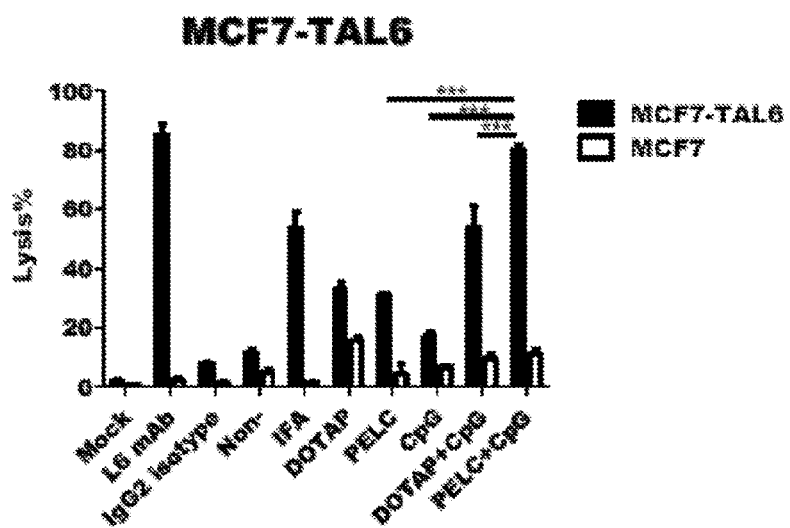

Chimeric Peptide Th-A2-5-EP1 Formulated with PELC/CpG Induced Antibody-Mediated Cellular Cytotoxicity Against Human Cancer Cells Mice were immunized with Th-A2-5-EP1 formulated with different adjuvants twice at a two-week interval. Sera was collected at 6 weeks for ADCC assay. Human lung cancer cell line H2981, as well as breast cancer cell lines MCF7 and MCF7-TAL6 were used as target cells. TAL6-specific ADCC was determined by Cr51 release assay. The lysis percentage was calculated by subtracting the lysis percentage of immunization serum from that of nave serum. As shown in FIG. 9, Th-A2-5-EP1 formulated with PELC/CpG had the strongest cytotoxicity against the cancer cells.

Antibody-Binding Region of EP1 was Identified Using Alanine Scanning

Figure 10:
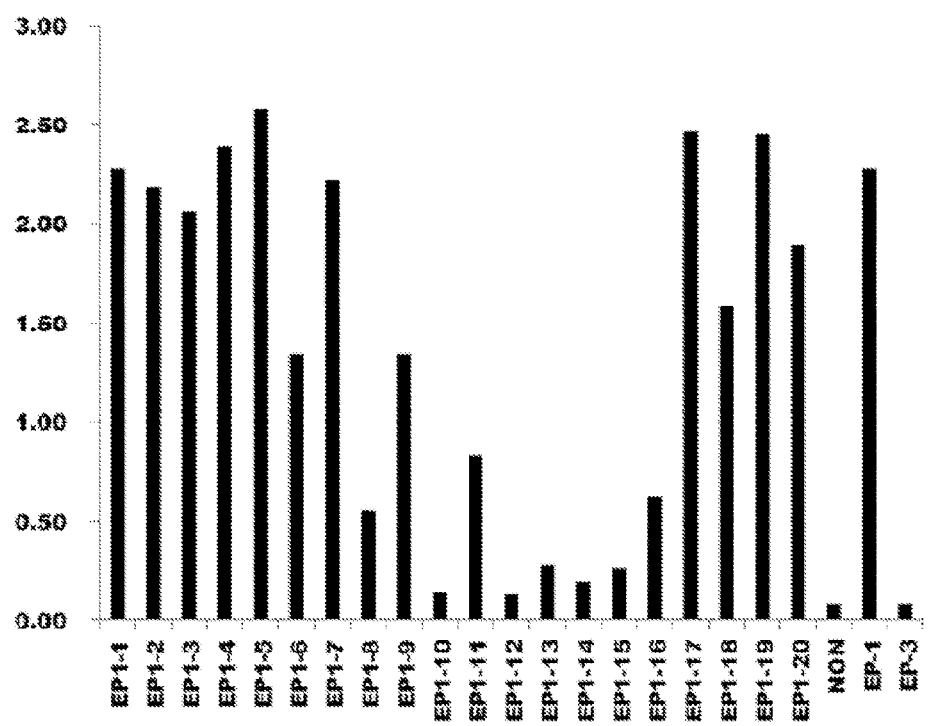
FIG. 10 is a graph showing identification of residues in EP1 that are important for antibody binding using alanine scanning. The amino acid residues in EPI were individually replaced with alanine to generate EP1-1 to EP1-20 peptides. Monoclonal antibody L6 was used to detect these peptides. EP1 is a positive control and EP-3 is a negative control.

Amino acid residues 1-20 in EP1 were individually replaced with alanine to generate EP1-1 to EP1-20 peptides. Monoclonal antibody L6 was used to detect these peptides. Certain residues, when replaced with alanine, reduced antibody binding. See FIG. 10. The data showed that these residues are important for antibody binding.

Animals and Cell Lines

Female 6-week-old C57BL/6 mice were obtained from the National Laboratory Animal Center, Taiwan. The HLA-A2 transgenic mice were kindly provided by Dr. Show-Li Chen (National Taiwan University, Taiwan) and housed in the Laboratory Animal Center of the National Health Research Institutes, Taiwan. All animal experiments were performed in specific pathogen-free (SPF) conditions under protocols approved by the Animal Committee of the National Health Research Institutes (NHRI).

The B16F1 cells stably expressed TAL6 (B16-L6), and then were transfected with the HLA-A2 gene to generate a stable cell line B16-L6-A2. The B16-L6-A2 and MCF-7-TAL6 cells were cultured in DMEM medium supplemented with 10% fetal bovine serum (FBS), 50 units/mL penicillin/streptomycin, 0.5 mM sodium pyruvate, 20 mM HEPES (Biological industries, Beit Haemek, Israel) at 37° C. in 5% $CO_2$ See Tu et al., Journal of immunotherapy, 35 (2012) 235-244. The EL4-L6-A2 and EL4-L6 cells were cultured in RPMI-1640 medium supplemented with 10% FBS.

Preparation of Monoclonal Antibodies

Hybridoma producing anti-TAL6 antibody (L6) was obtained from the American Type Culture Collection. 1F4 and 9C7 anti-TAL6 monoclonal antibodies were generated from BALB/c mice immunized with human TAL6 plasmid DNA as described. Monoclonal antibodies were purified by Protein A affinity chromatography using high salt conditions as described. See Chang et al., Int J Cancer, 116 (2005) 243-252.

Antibody concentrations were determined by Micro BCA protein Assay Kit (PIERCE).

ELISA

For antibody epitope mapping, L6, 9C7 and 1F4 Mabs were assayed by ELISA. For assaying EP1 titers of the specific antibodies, antisera were collected from the mice immunized with EP1 peptide, and the titers of the specific antibodies were assayed by ELISA. The 96 well assay plates were coated with peptide (1 µg/ml) or cell ($2\times10^6$). After blocking with 5% BSA-PBS, the antisera (1:1000 v/v) were diluted with 5% BSA-PBS and added to the plate for 1 hour. HRP-conjugated goat anti-mouse IgG (1:4000 v/v) was used to detect EP1 antibody titer. The TMB peroxidase EIA substrate was added, which was stopped with 1N $H_2SO_4$. Absorbance was measured at 450 nm.

Animal Study

HLA-A2 Tg mice were injected subcutaneously (s.c.) twice at a 2-week interval with peptide formulated in IFA, alum, DOTAP liposome, PELC nanoparticles, or TLR9 agonist CpG. Seven days after the second immunization, the B16-L6-A2 or B16-L6 cells ($2\times10^4$) were inoculated s.c. on the opposite site of the peptide injection. Tumor sizes were measure 2-3 times per week. Tumor volume was calculated using the formula: tumor volume=length×width×width/2.

Antibody Dependent Cell-Mediated Cytotoxicity (ADCC)

Mice spleen cells were used as effector cells for the ADCC assay. Spleen cells were adjusted to a concentration of $8\times10^6$ cells/ml in LCM medium. Cells were added in tubes and then divided into aliquots (100 µl/well in 96-well plates). EL4-L6 or EL-4 target cells ($2\times10^7$/ml) were labeled with 100 µCi of $^{51}$C ($Na_2{}^{51}CrO4$, PerkinElmer, MA) at 37° C. for 1 hr. The $^{51}$Cr-labelled EL4-L6 or EL4 cells were adjusted to a concentration of $2\times10^5$ cells/ml in LCM medium and then TAL6 antiserum or nave mouse serum (1:10) was added. After 6 hr, supernatants were harvested to measure the radioactivity using a gamma counter. Spontaneous release was measured in wells containing target cells alone. Triton X-100 (2%) was used to lyse the target cells to estimate maximal release. Percent cytotoxicity was determined according to the formula: percent lysis=100×(experimental $^{51}$Cr release−spontaneous $^{51}$Cr release)/(maximal $^{51}$Cr release−spontaneous $^{51}$Cr release).

ELISPOT Assay

Spleen cells ($5\times10^5$) were mixed with 10 µg/ml of the indicated peptide and added to a 96-well PVDF-membrane plate coated with anti-IFN-γ antibody. The plates were then incubated in a humidified atmosphere of 5% $CO_2$ in air at 37° C. for 48 hours. After incubation, cells were removed by washing the plates 6 times with 0.05% (w/v) tween 20 in PBS. A 50 µl aliquot of biotinylated secondary anti-IFN-γ antibody (clone R46A2; eBioscience, San Diego, Calif.) was added to each well. After 2 hours, the plate was washed and streptavidin-HRP (eBioscience) was added. Spots were developed using a 3-amine-9-ethyl carbazole (AEC, Sigma) solution. The reaction was stopped after 4-6 minutes by running the plate under tap water. The spots were then counted using an ELISPOT reader (Cellular Technology Ltd., Shaker Heights, Ohio).

CD107a Cytotoxicity Assay

HLA-A2 Tg mice were injected s.c. twice with the indicated peptides (50 µg/ml) emulsified in IFA, DOTAP or PELC in the absence or presence of CpG ODN (10 µg/mouse). On day 7 after the second immunization, splenocytes were harvested and then resuspended to $2 \times 10^7$ cell/ml in medium that contained 10 µg/ml of the indicated peptides (50 µg/ml) or cells ($2 \times 10^6$ cell/ml) and PE-conjugated anti-mouse CD107a antibody (1:100) in 96-well round-bottom plates. After 2 hours at 37° C., brefeldin A (10 µg/ml) and monensin (0.66 µg/ml) were added for another 2-6 hours. The plates were washed with PBS containing 0.1% FBS, and anti-mouse Fc antibody (1:100) was added for 5 minutes, followed by addition of the FITC-conjugated anti-mouse CD8 antibody (1:100) for 30 minutes. The cytotoxic CD107a$^+$CD8$^+$ cells were analyzed on a fluorescence-activated cell sorter (FACS calibur, BD Bioscience).

Wound Healing Assay

Wound healing was investigated using a Culture-Insert (500 µm) (Ibidi). A 100 µl suspension of B16-L6 cells in DMEM-10% FBS ($5 \times 10^6$ cells/ml) was seeded into each well of the insert. After cell attachment for 24 h, the culture inserts were removed and the cells were incubated with antiserum (1:100 v/v) in DMEM-10% FBS. The cell migration into the defined cell free gap was observed for 48 hr as indicated under an inverted microscope. For assay analysis, cells were tracked using the manual tracking software component of the ImageJ programmer.

Statistical Analysis

The statistical significance of differences between the mean values of the experimental groups was determined using the student t test and ANOVA. The differences were considered statistically significant if the P value was <0.05.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. An immunogenic peptide, comprising the sequence of $X_1X_2X_3X_4X_5X_6X_7$CLDSLGQWN$X_8X_9X_{10}X_{11}$ (SEQ ID NO: 3), in which $X_1$ to $X_{11}$, individually, is an amino acid, wherein (i) $X_8$ is threonine, or (ii) the peptide further includes a helper T cell (Th) epitope that is AKFVAAWTLKAAA (SEQ ID NO: 7) or AQYIKANSKFIGITEL (SEQ ID NO: 8), the peptide having 100 or fewer amino acids.

2. The peptide of claim 1, wherein the peptide has the sequence of SEQ ID NO: 3 in which $X_8$ is threonine.

3. The peptide of claim 1, wherein the peptide further includes a CTL epitope that is LLMLLPAFV (SEQ ID NO: 5) or RFVWFFSGI (SEQ ID NO: 6).

4. The peptide of claim 1, wherein the peptide further includes the Th epitope.

5. The peptide of claim 1, further comprising a linker sequence between two of the epitopes.

6. The peptide of claim 5, wherein the peptide contains the sequence of AKFVAAWTLKAAAAAALLMLL-PAFVAAAGLAEGPLCLDSLGQWNYTFA (SEQ ID NO: 9).

7. A nucleic acid molecule comprising a sequence that encodes the peptide of claim 1.

8. The nucleic acid molecule of claim 7, wherein the nucleic acid molecule is an expression vector capable of expressing the peptide.

9. An immunogenic composition comprising the peptide of claim 1.

10. The immunogenic composition of claim 9, further comprising an adjuvant.

11. The immunogenic composition of claim 10, wherein the adjuvant is selected from the group consisting of incomplete Freund's adjuvant (IFA), DOTAP, PELC, and unmethylated CpG-containing oligodeoxynucleotides (CpG).

12. The immunogenic composition of claim 11, wherein the composition contains PELC and CpG, and the peptide has the sequence of AKFVAAWTLKAAAAAALLMLL-PAFVAAAGLAEGPLCLDSLGQWNYTFA (SEQ ID NO: 9).

13. An immunogenic composition comprising the nucleic acid molecule of claim 7.

14. The immunogenic composition of claim 13, further comprising an adjuvant.

15. A method of treating a cancer in a subject, the method comprising administering to a subject in need thereof the immunogenic composition of claim 9.

16. The method of claim 15, wherein the cancer has cells that express TAL6.

17. The method of claim 16, wherein the cancer is lung cancer, colon cancer, breast cancer, ovarian carcinoma, gastric cancer, Kaposi's sarcoma, hepatoma, pancreatic cancer, cervical cancer, endometrial cancer, head and neck cancer, ovarian cancer, or prostate cancer.

* * * * *